(12) United States Patent
O'Fallon (10) Patent No.: US 10,813,689 B2
(45) Date of Patent: Oct. 27, 2020

(54) ABLATION CATHETER WITH RADIAL FORCE DETECTION

(71) Applicant: Biosense Webster (Israel) Ltd., Yokneam (IL)

(72) Inventor: Patrick O'Fallon, Toluca Lake, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1098 days.

(21) Appl. No.: 14/951,907

(22) Filed: Nov. 25, 2015

(65) Prior Publication Data
US 2017/0143412 A1    May 25, 2017

(51) Int. Cl.
*A61B 18/14* (2006.01)
*A61B 18/00* (2006.01)
*A61B 90/00* (2016.01)

(52) U.S. Cl.
CPC .. *A61B 18/1492* (2013.01); *A61B 2018/0016* (2013.01); *A61B 2018/00029* (2013.01); *A61B 2018/00267* (2013.01); *A61B 2018/00357* (2013.01); *A61B 2018/00577* (2013.01); *A61B 2018/00875* (2013.01); *A61B 2090/065* (2016.02); *A61B 2218/002* (2013.01)

(58) Field of Classification Search
CPC .......... A61B 2090/065; A61B 18/1492; A61B 2018/00029; A61B 2018/0016; A61B 2018/00267; A61B 2018/00357; A61B 2018/00577; A61B 2018/00875; A61B 2218/002
See application file for complete search history.

(56) References Cited

U.S. PATENT DOCUMENTS

| | | | |
|---|---|---|---|
| 3,888,117 A | 6/1975 | Lewis | |
| 4,274,423 A * | 6/1981 | Mizuno | A61B 5/0215 600/488 |
| 5,391,199 A | 2/1995 | Ben-Haim | |
| 5,972,030 A * | 10/1999 | Garrison | A61B 18/1492 623/2.11 |
| 6,019,728 A | 2/2000 | Iwata et al. | |
| 6,239,724 B1 | 5/2001 | Doron et al. | |
| 6,332,089 B1 | 12/2001 | Acker et al. | |
| 6,468,260 B1 | 10/2002 | Bumbalough et al. | |
| 6,484,118 B1 | 11/2002 | Govari | |
| 6,500,167 B1 | 12/2002 | Webster, Jr. | |

(Continued)

FOREIGN PATENT DOCUMENTS

| | | |
|---|---|---|
| EP | 2664295 A1 | 11/2013 |
| WO | 9605768 A1 | 2/1996 |

OTHER PUBLICATIONS

European Search Report from corresponding European Patent Application 16200409.7, dated May 12, 2017, pp. 1-8.

*Primary Examiner* — Eun Hwa Kim
*Assistant Examiner* — Catherine Premraj
(74) *Attorney, Agent, or Firm* — Dergosits & Noah LLP; Todd A. Noah (57) ABSTRACT

Systems and methods are disclosed for providing and using an ablation catheter. The catheter may include a ring electrode having a contact force sensor that provides signals to a system controller to indicate whether the ablation electrode is in contact with the tissue to be ablated as well as how much of the ablation electrode is in contact with the tissue.

18 Claims, 6 Drawing Sheets

(56) References Cited

U.S. PATENT DOCUMENTS

| | | | |
|---|---|---|---|
| 6,522,933 | B2 | 2/2003 | Nguyen |
| 6,618,612 | B1 | 9/2003 | Acker et al. |
| 6,690,963 | B2 | 2/2004 | Ben-Haim et al. |
| 7,662,151 | B2 | 2/2010 | Crompton, Jr. et al. |
| 7,731,664 | B1 | 6/2010 | Millar |
| 8,209,031 | B1 | 6/2012 | Rodriguez et al. |
| 8,613,231 | B2 | 12/2013 | Muroyama et al. |
| 8,617,087 | B2 | 12/2013 | Schultz |
| 2002/0065455 | A1 | 5/2002 | Ben-Haim et al. |
| 2002/0123749 | A1 | 9/2002 | Jain |
| 2003/0120150 | A1 | 6/2003 | Govari |
| 2004/0068178 | A1 | 4/2004 | Govari |
| 2004/0176754 | A1* | 9/2004 | Island ............... A61B 18/203 606/9 |
| 2012/0259194 | A1 | 10/2012 | Selkee |
| 2013/0060245 | A1* | 3/2013 | Grunewald ........ A61B 18/1492 606/41 |
| 2014/0336640 | A1* | 11/2014 | Beeckler ........... A61B 18/1492 606/41 |
| 2015/0265334 | A1* | 9/2015 | Franke .............. A61B 18/1206 606/34 |
| 2015/0300895 | A1* | 10/2015 | Matsudate ......... A61B 18/1492 73/777 |
| 2015/0359484 | A1* | 12/2015 | Bitzer ............... A61B 18/1492 600/372 |

\* cited by examiner

ABLATION CATHETER WITH RADIAL FORCE DETECTION

FIELD OF THE PRESENT DISCLOSURE

This disclosure relates generally to methods and devices for percutaneous medical treatment, and specifically to catheters, in particular, ablation catheters. More particularly, this disclosure relates to ablation catheters designs that have radial force detection sensors connected to the ablation electrode.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a single or multi-electrode catheter into a renal artery in order to complete a helical or circumferential lesion in the artery in order to denervate the artery for the treatment of hypertension.

In such procedures, a reference electrode is typically provided and may be attached to the skin of the patient or by means of a second catheter. RF current is applied to the electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue.

During the ablation procedure, it is important for a practitioner to know when the electrode is adjacent to and in contact with the tissue to be ablated. For those catheter designs having a single electrode at the tip, a force feedback device is used to let the practitioner know whether the tip is in contact with the tissue, how far that tip is within the tissue and provide better electrical feedback. However, for multi-electrode devices a force feedback sensor is not available to provide similar information for each of the electrodes located along the length of the catheter.

Accordingly, it would be desirable to provide a multi-electrode ablation catheter that has a feedback controller that provides contact information for each of the individual electrodes. As will be described in the following materials, this disclosure satisfies these and other needs.

SUMMARY

The present disclosure is directed to a catheter having an elongated body, at least one electrode disposed on an intermediate portion of the elongate body and at least one contact force sensor assembly connected to the at least one ring electrode.

In one aspect the contact force sensor assembly includes a detent and a strain gauge, the strain gauge is attached to the detent. Further, the strain gauge includes a circuit and at least one wire to electrically link the circuit to a system controller.

In one aspect, the detent comprises a semicircular portion connected to a flange portion. Further, the detent is disposed within a correspondingly shaped opening in a wall of the electrode.

In one aspect, the strain gauge further comprises a first attachment portion and a second attachment portion. In this aspect, the first attachment portion is for connecting the wire of the contact force sensor and the second attachment portion for securing the strain gauge to an inner wall of the electrode.

In one aspect, at least one electrode comprises an RF ablation electrode with a plurality of irrigation apertures formed through the wall of the electrode. Further, the catheter may be a multi-electrode catheter configured to form a helical shape, a lasso or a basket when deployed. Still further, the catheter may include a deflectable tip as well as a tip electrode.

In one aspect, the electrode may further include three contact force sensors, each being evenly spaced about a circumference of the electrode.

This disclosure is also directed to a method for the ablation of a portion of tissue of a patient by an operator. The method includes inserting a catheter into the patient. The catheter includes an elongated body, at least one electrode disposed on an intermediate portion of the elongate body, at least one contact force sensor assembly connected to the electrode and a plurality of irrigation apertures formed in a wall of the at least one electrode. The method further includes connecting the catheter to a system controller capable of receiving signals from a plurality of sensors, delivering power to the at least one electrode, and controlling the power to the at least one electrode to ablate the tissue based at least in part on measurements from the plurality of sensors.

In one aspect, the method also includes determining contact of the electrode with tissue and estimating a degree of contact of the electrode with tissue based on measurements from the at least one contact force sensor.

This disclosure is also directed to a system for the ablation of a portion of tissue includes a catheter having an elongated body, at least one electrode disposed on an intermediate portion of the elongate body, at least one contact force sensor assembly operably connected to the at least one ring electrode, and a plurality of irrigation apertures formed in a wall of the at least one electrode. The system also includes a system controller capable of receiving signals from a plurality of sensors, delivering power to the at least one electrode and controlling the power to the at least one electrode to ablate tissue. Further, the system controller receives signals from the contact force sensor to indicate the degree of contact of the at least one electrode to the tissue to be ablated.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Figure 1:
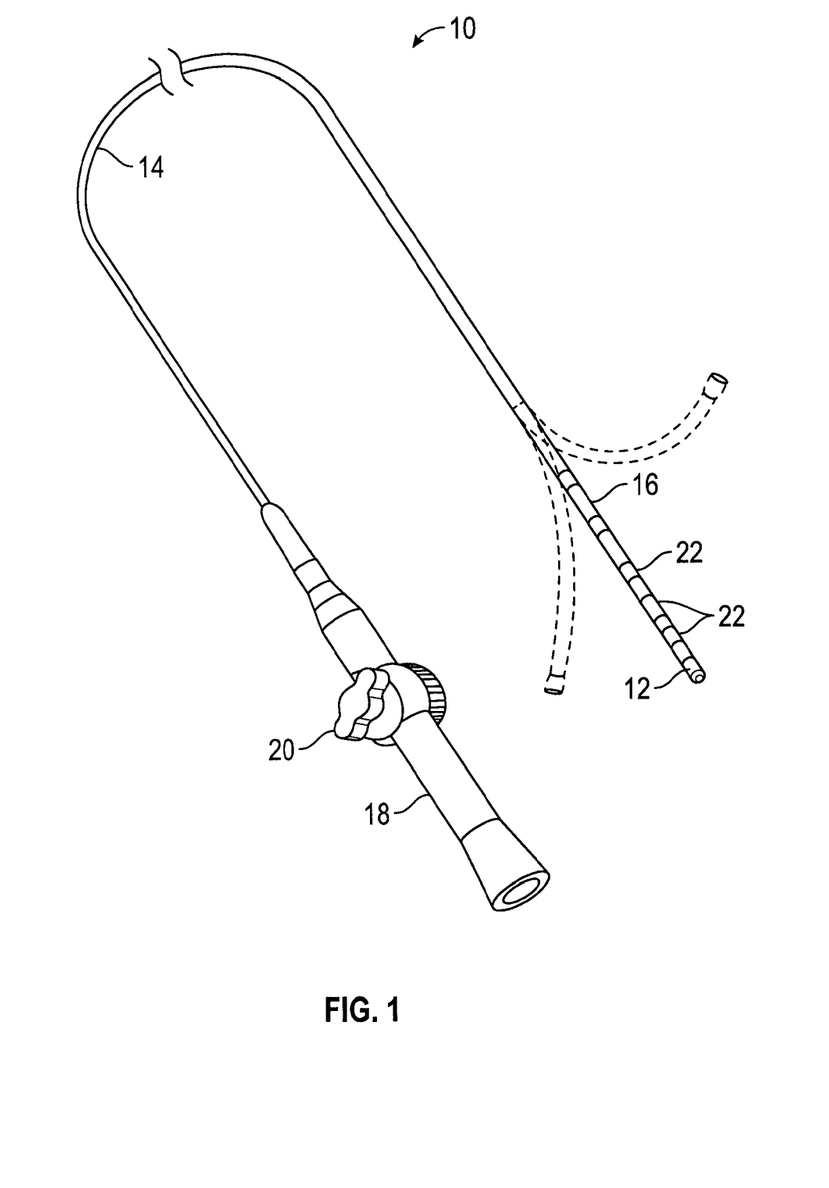
FIG. 1 is a perspective view of a catheter in accordance with an embodiment of the present invention.

As illustrated in FIG. 1, the present disclosure includes a multi-electrode ablation catheter 10 with a distal tip section that includes tip electrode 12 adapted for contact with target tissue. Catheter 10, according to the disclosed embodiments, comprises an elongated body that includes an insertion shaft or catheter body 14 having a longitudinal axis, and an intermediate section 16 distal of the catheter body having multiple ring electrodes 22 disposed along its length. Ring electrodes 22 are also adapted for contact with target tissue.

In one embodiment, catheter 10 may be used either as a single tip electrode or it may be deployed in an arc to be used as a multi-electrode catheter. In this embodiment, intermediate section 16 may be uni- or bi-directionally deflectable off-axis from the catheter body, as indicated, to provide the arc needed to position the electrodes to ablate the tissue in an arcuate pattern. Proximal of catheter body 14 is control handle 18 that allows an operator to maneuver the catheter, which may include deflecting intermediate section 14 when a steerable embodiment is employed. In an example, control handle 18 may include deflection knob 20 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, and 6,522,933 and U.S. patent application Ser. No. 12/960,286, filed Dec. 3, 2010, the entire disclosures of which are incorporated herein by reference.

Catheter body 14 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 14 so that, when the control handle 20 is rotated, the intermediate section 16 will rotate in a corresponding manner. Depending upon the intended use, the outer diameter of catheter body 14 may be approximately 8 french, and in some embodiments, may be 7 french. Likewise the thickness of the outer wall of catheter body 14 may be thin enough so that a central lumen may accommodate any desired wires, cables and/or tubes. The useful length of the catheter, i.e., that portion that can be inserted into the body may vary as desired. In exemplary embodiments, the useful length may range from about 110 cm to about 120 cm. The length of the intermediate section 16 may correspond to a relatively small portion of the useful length, such as from about 3.5 cm to about 10 cm, and in some embodiments, from about 5 cm to about 6.5 cm.

Figure 2:
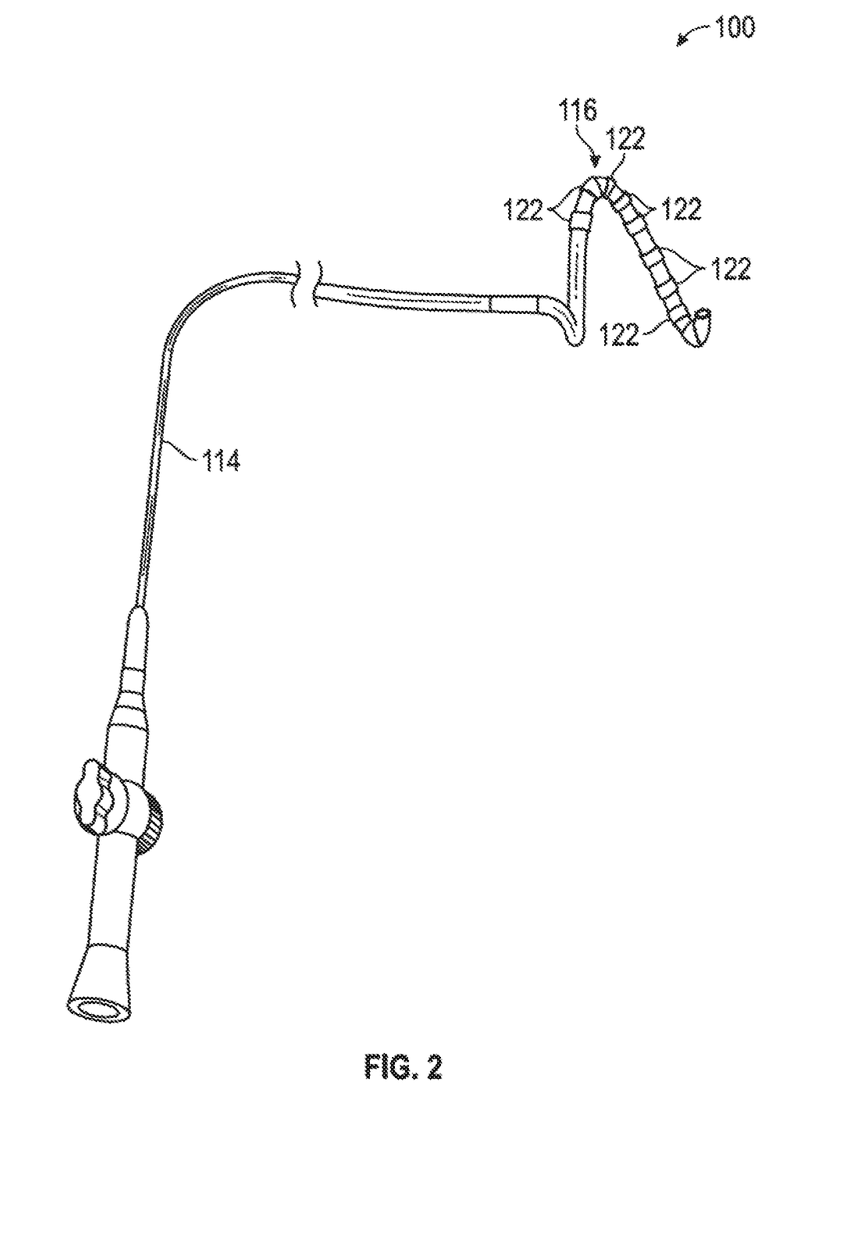
FIG. 2 is a perspective view of a helical multi-electrode assembly at the distal end of the catheter of FIG. 1, in accordance with another embodiment of the present invention.

FIG. 2 illustrates another embodiment of a multi-electrode catheter 100, in accordance with another embodiment of the invention. In this embodiment, catheter 100, comprises an elongated body that includes an insertion shaft or catheter body 114 having a longitudinal axis, and an intermediate section 116 distal of the catheter body. In this embodiment, as contrasted with the embodiment of FIG. 1, all of the electrodes are located proximal to the distal tip of the catheter. Here, a series of ring electrodes 122 are disposed along the length of intermediate section 116. Ring electrodes 122 are adapted for contact with target tissue. In this embodiment, intermediate section 116 forms a helical shape once it is deployed at the treatment site. In this embodiment, ring electrodes 122 form a helical lesion pattern when activated. All other aspects of this embodiment are similar to those stated above for the embodiment illustrated in FIG. 1. In this embodiment the catheter is French 8,9,11, or 12 French.

Figure 3:
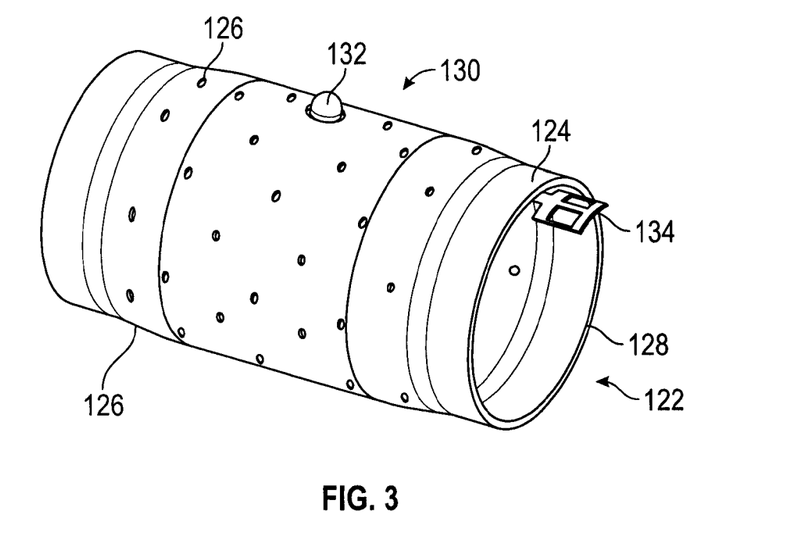
FIG. 3 is a perspective view of an electrode with a contact force sensor in accordance with an embodiment of the present invention.

Turning now to FIG. 3, what is illustrated is one embodiment of a ring electrode including a contact force sensor 130. FIGS. 4-7 illustrate the details of contact force sensor assembly 130. Referring back to FIG. 3, ring electrode may be electrode 12 or 122 illustrated in FIGS. 1 and 2, respectively. For simplicity, ring electrode will be referred to as ring electrode 122 though any ring electrode as is known in the art may be adapted with the current invention. Ring electrode 122 is configured as an elongated, generally cylindrical portion 124 having a plurality of irrigation apertures 126. Irrigation apertures 126 may be used for irrigating the tissue as it is ablated. The shell of electrode 122 defines an interior cavity 128 that is in fluid communication with a lumen extending the length of catheter body 114 (not shown) to supply irrigation fluid. A plurality of irrigation apertures 126 are distributed substantially evenly across the surface of electrode 122, through which fluid entering and filling the cavity may exit to outside of the electrode 122, to provide cooling of electrode 122 and the environment adjacent electrode 122 as desired. The shell of electrode 122 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

Figure 4:
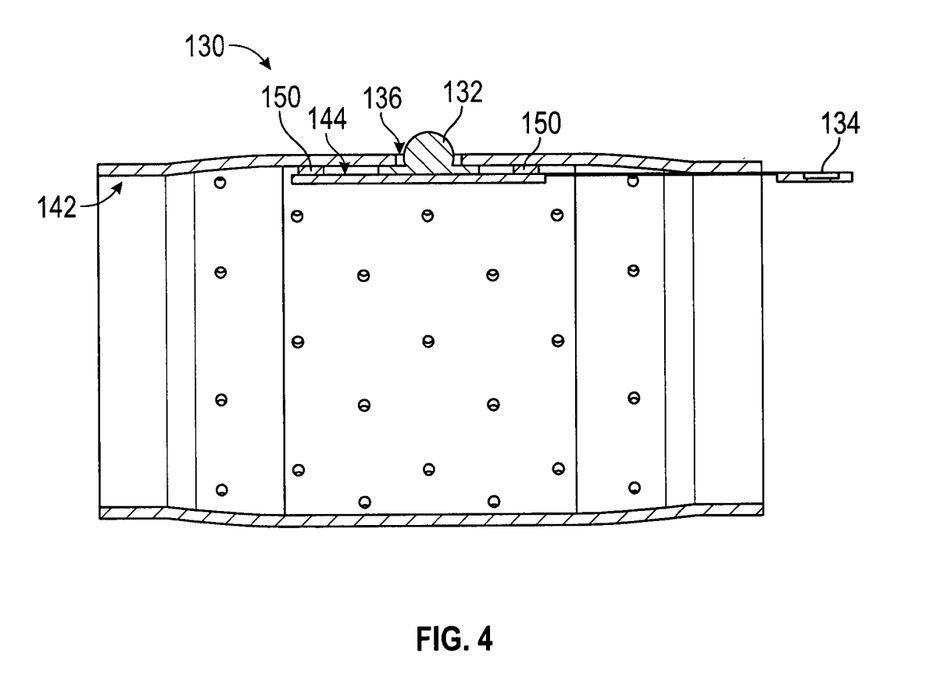
FIG. 4 is a cross-sectional view of the contact force sensor of FIG. 3, in accordance with an embodiment of the present invention.
Figure 5:
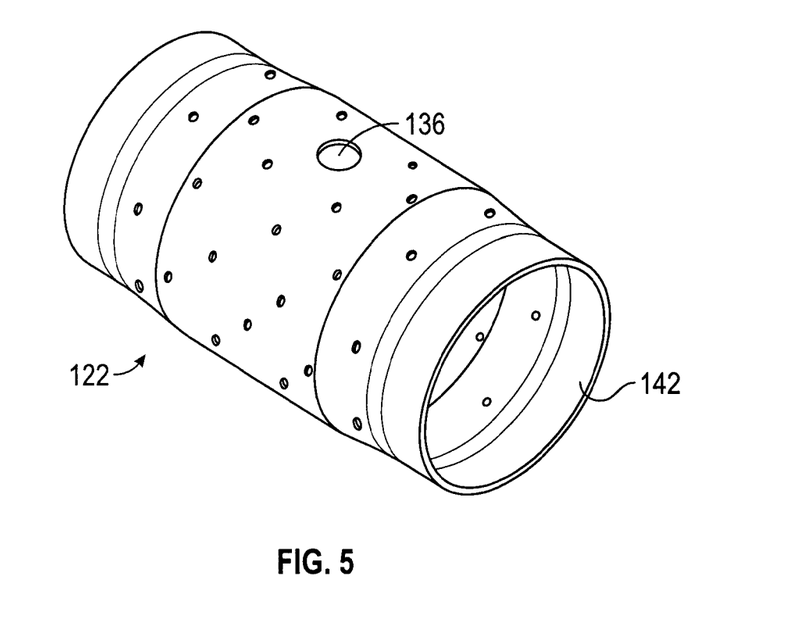
FIG. 5 is a perspective view of the ring electrode of FIG. 3, in accordance with an embodiment of the present invention.
Figure 7:
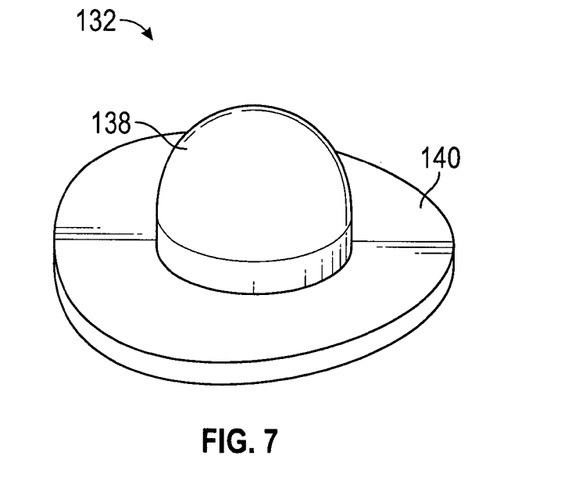
FIG. 7 is a perspective view of the detent of FIG. 3, in accordance with an embodiment of the present invention.

Disposed within ring electrode 122 is contact force sensor 130. Contact force sensor assembly 130 includes a detent 132 and a strain gauge 134. FIG. 7 illustrates one embodiment of detent 132. In this embodiment, detent 132 includes a semicircular contact portion 138 and a flange portion 140 connected to contact portion 138. Contact portion 138 is essentially dome-shaped and protrudes through an opening 136 located within the shell of ring electrode 122. Opening 136 allows for radial movement of the detent when exposed to a force from contact with the lumen of a vessel or organ, as described in more detail below. As best illustrated in FIG. 4, flange portion 140 is disposed between the interior wall 142 of the shell of the ring electrode 132 and top surface 144 of strain gauge 134. Flange portion 140 acts as an anchor to keep the detent disposed within ring electrode 122. Alternatively, the flange portion 140 may be removed and the contact portion is adhered directly to the starin gauge 134. Detent 132 may be made of any suitable material such as acetal polymers, polyether ether ketone ("PEEK"), polycarbonate or acrylonitrile butadiene styrene ("ABS"). In another embodiment, detent 132 is fashioned as a polymeric ball with a complementarily shaped opening 136 to retain the ball-shaped detent within the electrode. Those with skill in the art will appreciate that the shape of the detent and corresponding opening may vary from the circular shape described above. In an example, the detent may be an elongated dome-shaped oval with a corresponding opening within the shell of the electrode.

Figure 6:
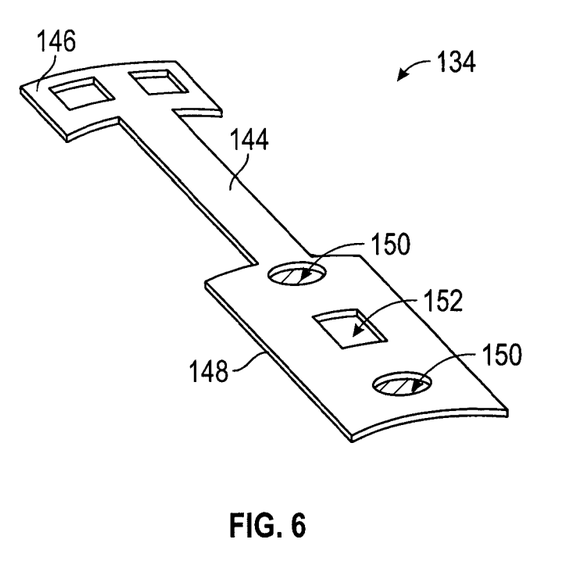
FIG. 6 is a perspective view of the strain gauge of FIG. 3, in accordance with an embodiment of the present invention.

As shown in FIG. 4, strain gauge 134 is an elongated structure that is attached to the interior wall 142 of electrode 122. Strain gauge 134 may be made of any suitable material where the strain rate is known, such as, polyamide or a metal such as Nitinol. Referring now to FIG. 6, the shape of strain gauge 134 has a radius of curvature that is complementary to the interior wall 142 of ring electrode 122, but a pliable material, such as polyimide, can be used and will conform to the interior wall of the ring electrode. Strain gauge 134 includes a first attachment portion 146 and a second attachment portion 148. Strain gauge 134 is attached to electrode 122 by any method known in the art such as by gluing, soldering, or welding. In one embodiment, strain gauge 134 is attached by soldering the strain gauge 134 to electrode 122 at soldering pads 150. In other embodiments, instead of soldering, the strain gauge includes areas of bare metal to be used in resistance welding the strain gauge to the electrode.

Strain gauge 134 further includes an embedded circuit 152 for determining the radial force applied to detent 132. Circuit 152 is electrically connected via wires to a system controller, described in more detail below. Suitable wires are connected to the strain gauge at first attachment portion 146. In practice, detent 132 engages the strain gauge 134 when exposed to a radial force. As the detent 132 is forced in a radial direction due to contact with the tissue, the detent 132 pushes down on strain gauge 134 causing the strain gauge to elongate along its longitudinal axis. As the strain gauge elongates, current passing through circuit 152 embedded within the strain gauge will send electrical signals to the system controller to indicate the radial force acting on the detent. With this feedback, the practitioner will determine whether or not the electrode is in contact with the tissue. Thin section 144 is used to bring the wires of the internal circuitry of the strain gage located at second attachment portion 148 to the outside of the ring electrode where the wires will be terminated at the first attachment portion 146.

Figure 8:
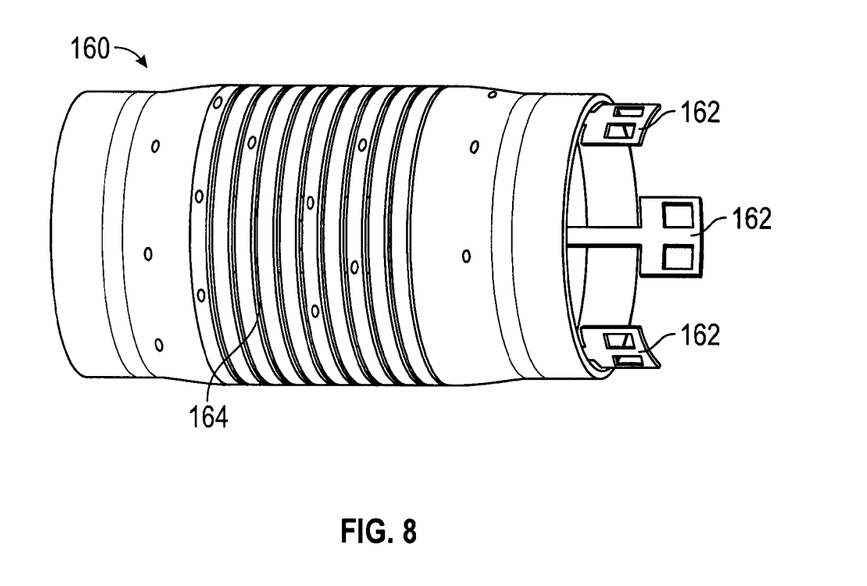
FIG. 8 is a perspective view of a ring electrode having a plurality of contact force sensor assemblies in accordance with another embodiment of the present invention.

Referring now to FIG. 8, illustrated is another embodiment of a ring electrode having at least one contact force sensor in accordance with the invention. In this example, ring electrode 160 includes three contact force sensor assemblies 162 each radially spaced by approximately 120 degrees around ring electrode 160. In this embodiment, the force sensors are equally spaced, but in other embodiments the force sensors may be staggered. The ring electrode further includes reliefs 164 cut around the diameter of the ring to enable the ring to deflect itself and the strain gauges attached along the inside surface of the ring. In this embodiment, no detents are required. Those with skill in the art will appreciate that the number of contact force sensor assemblies may vary from one to a plurality depending on the purpose of the catheter in use by the practitioner. For example, if the catheter is deflectable in multiple directions, the ring electrodes may include contact force sensors for each direction opposite of the direction of deflection.

As will be appreciated, the catheters mentioned above will include additional structures not described or illustrated for the sake of clarity. For example, ablation catheter 10 will include those structures necessary for ablation such as a conduit for receiving an RF coil to be used to energize electrode 12, 22. Other conduits may be used for any suitable purpose, including routing and/or anchoring safety wire to facilitate retrieval of the electrode assembly or other distal portions of catheter 10 should they become detached during a procedure. Safety wire may be formed from Vectran™ or other suitable materials. In other embodiments, one or more conduits may accommodate electromagnetic position sensors that may be used in conjunction with a mapping system to aid visualization of the placement of the distal end of catheter 10 within a patient's anatomy along with the contact force sensing system described above in relation to FIGS. 1 to 8.

In comparison to conventional RF ablation catheters, the techniques of this disclosure represent notable benefits. Contact force sensing catheters, as described above, are capable of demonstrating contact with tissue and provide an indication as to how much force is detected. Typically, the recorded force goes from 0 grams, i.e., no contact with the tissue, to a maximum of 50 grams of force detected. Preferably, the recorded force is about 30 grams. Additionally, each of the contact force sensors of a multi-electrode catheter will provide individual feedback as to whether each electrode is in contact with the tissue. With the feedback information provided, a practitioner will be able to make the necessary adjustments to achieve the desired ablation at the treatment site.

Figure 9:
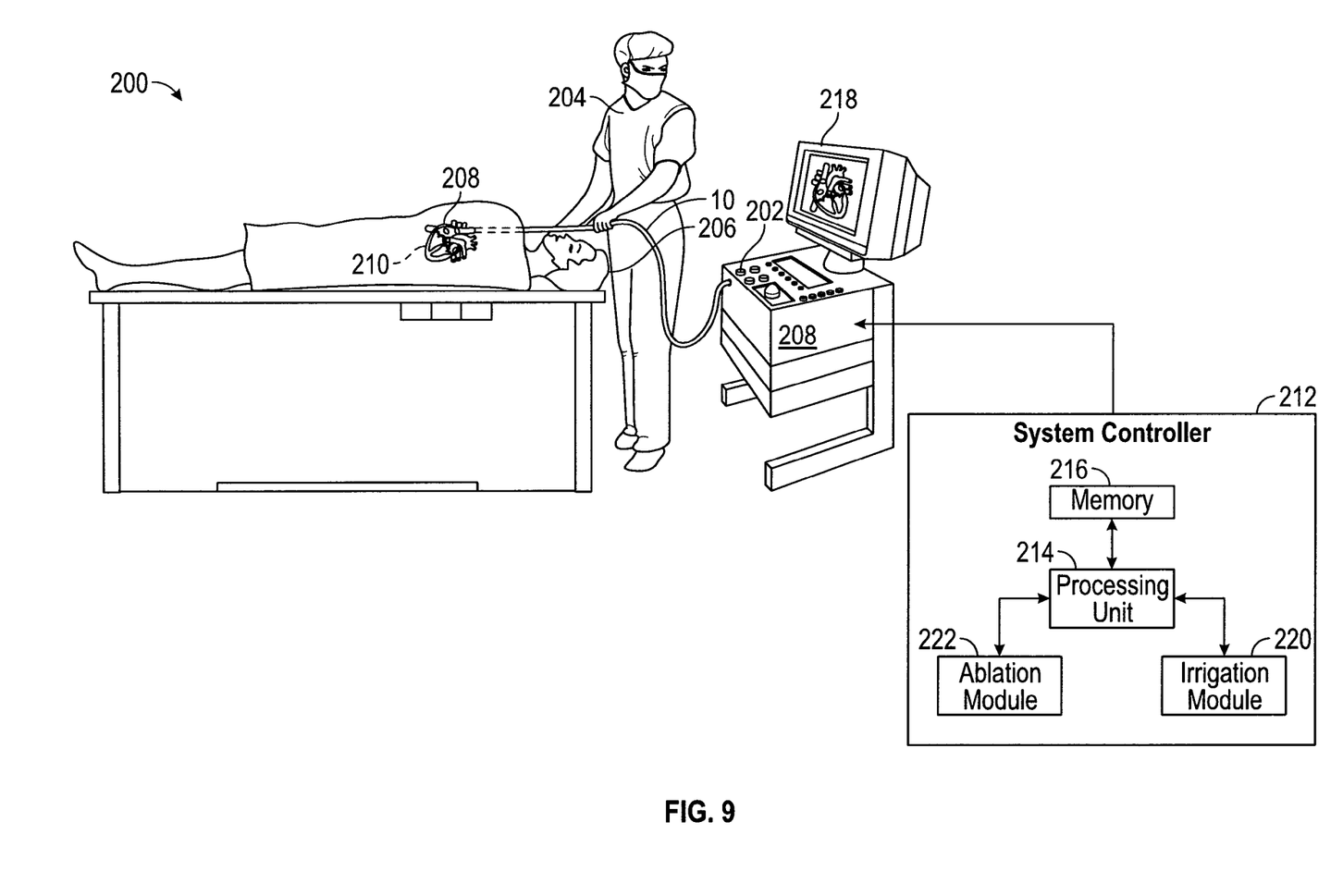
FIG. 9 is a schematic view of an ablation system in accordance with an embodiment of the present invention.

Use of multi-electrode catheter 10 in an ablation procedure may follow techniques known to those of skill in the art. FIG. 9 is a schematic, pictorial illustration of a system 200 for renal and/or cardiac catheterization and ablation, in accordance with an embodiment of the present invention. System 200 may be based, for example, on the CARTO™ mapping systems, produced by Biosense Webster Inc. (Diamond Bar, Calif.) and/or SmartAblate or nMarq RF generators. This system comprises an invasive probe in the form of catheter 10 and a control and/or ablation console 202. An operator 204, such as a cardiologist, electrophysiologist or interventional radiologist, inserts ablation catheter 10 into and through the body of a patient 206, such as through a femoral or radial access approach, so that a distal end of catheter 10, in particular, electrode 12, engages tissue at a desired location or locations, such as a chamber of heart 208 of patient 206. Catheter 10 is typically connected by a suitable connector at its proximal end to console 202. Console 202 comprises a RF generator 208, which supplies high-frequency electrical energy via the catheter for ablating tissue 210 at the locations engaged by electrode 22.

Console 202 may also use magnetic position sensing to determine position coordinates of the distal end of catheter 10 inside the body of the patient 206. For this purpose, a driver circuit in console 202 drives field generators to generate magnetic fields within the body of patient 206. Typically, the field generators comprise coils, which are placed below the patient's torso at known positions external to the patient. These coils generate magnetic fields in a predefined working volume that contains the area of interest. A magnetic field sensor (not shown) within distal end of catheter 10 generates electrical signals in response to these magnetic fields. A signal processor in console 202 may process these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Console 202 may include system controller 212, comprising a processing unit 216 communicating with a memory 214, wherein is stored software for operation of system 200. Controller 212 may be an industry standard personal computer comprising a general purpose computer processing unit. However, in some embodiments, at least some of the functions of the controller are performed using custom designed application specific integrated circuits (ASICs) or a field programmable gate array (FPGA). Controller 212 is typically operated by the operator 204 using suitable input peripherals and a graphic user interface (GUI) 218 which enable the operator to set parameters of the system 200. GUI 218 typically also displays results of the procedure to the operator. The software in memory 214 may be downloaded to the controller in electronic form, over a network, for example. Alternatively or additionally, the software may be provided on non-transitory tangible media such as optical, magnetic or electronic storage media. In some embodiments, one or more contact force sensors may send signals to console 202 to provide an indication of the pressure on electrode 22. Signals from contact force sensor wires may be provided to system controller 212 to obtain measurements from strain gauge 134. Such signals may be used to provide to the physician the level of tissue contact of each individual electrode. Additionally, the system controller 212 will provide an indication as to which of the multi-electrodes are in contact with the tissue to be ablated. With this feedback information, the practitioner will be able to make the necessary adjustments to ensure a complete ablation. As noted above, this invention is well suited for any multi-electrode catheter such as, for example, those having a lasso, arcuate, helical or basket configuration of ring electrodes.

Typically, during an ablation, heat is generated by the RF energy in the tissue of the patient to effect the ablation and some of this heat is reflected to the electrode 12 causing coagulation at and around the electrode. System 200 irrigates this region through irrigation apertures 26 and the rate of flow of irrigation is controlled by irrigation module 220 and the power (RF energy) sent to electrode 22 is controlled by ablation module 222. Further, the percentage of the surface of electrode 22 that is coupled with tissue may be estimated based on the contact force observed. As yet another example, additional sensors of catheter 10 may provide intracardiac electrocardiograms to system controller 212, to be used for determining when the tissue site being ablated is no longer conducting arrhythmogenic currents.

Described herein are certain exemplary embodiments. However, one skilled in the art that pertains to the present embodiments will understand that the principles of this disclosure can be extended easily with appropriate modifications to other applications.

What is claimed is:

1. A catheter, comprising:
   an elongated body;
   at least one electrode disposed on an intermediate portion of the elongated body; and
   at least one contact force sensor assembly operably connected to the at least one electrode, the at least one contact force sensor assembly comprising a strain gauge, the strain gauge having a radius of curvature that is complementary to an interior wall of the at least one electrode, and a detent operably attached to the strain gauge, the detent being disposed within and extending through a correspondingly shaped opening in a wall of the at least one electrode.

2. The catheter of claim 1, wherein the strain gauge further comprises:
   a circuit; and
   at least one wire, the at least one wire electrically linking the circuit to a system controller.

3. The catheter of claim 1, wherein the detent comprises a semicircular portion operably connected to a flange portion.

4. The catheter of claim 2, wherein the strain gauge further comprises a first attachment portion and a second attachment portion, the first attachment portion for connecting the at least one wire and the second attachment portion for securing the strain gauge to the interior wall of the at least one electrode.

5. The catheter of claim 1, wherein the at least one electrode comprises an RF ablation electrode.

6. The catheter of claim 5, wherein the at least one electrode further comprises a plurality of irrigation apertures, the plurality of irrigation apertures formed through the wall of the at least one electrode.

7. The catheter of claim 5, wherein the catheter is a multi-electrode catheter comprising a plurality of electrodes, the plurality of electrodes configured to form a helical pattern when deployed.

8. The catheter of claim 5, wherein the catheter is a multi-electrode catheter comprising a plurality of electrodes, the plurality of electrodes configured to form a lasso when deployed.

9. The catheter of claim 5, wherein the catheter is a multi-electrode catheter comprising a plurality of electrodes, the plurality of electrodes configured to form a basket when deployed.

10. The catheter of claim 1, wherein the at least one electrode further comprises three contact force sensors, the contact force sensors evenly spaced about a circumference of the at least one electrode.

11. The catheter of claim 1 wherein the catheter is a deflectable catheter.

12. The catheter of claim 1, wherein the catheter further comprises a tip electrode.

13. A method for the ablation of a portion of tissue of a patient by an operator comprising:
    inserting a catheter into the patient, wherein the catheter comprises:
        an elongated body;
        at least one electrode disposed on an intermediate portion of the elongated body;
        at least one contact force sensor assembly operably connected to the at least one electrode, the at least one contact force sensor assembly comprising a strain gauge,
        the strain gauge having a radius of curvature that is complementary to an interior wall of the at least one electrode, and a detent operably attached to the strain gauge,
        the detent being disposed within and extending through a correspondingly shaped opening in a wall of the at least one electrode; and
        a plurality of irrigation apertures formed in a wall of the at least one electrode;
    connecting the catheter to a system controller capable of receiving signals from a plurality of sensors and delivering power to the at least one electrode; and
    controlling the power to the at least one electrode to ablate tissue.

14. The method of claim 13, wherein controlling the power to the at least one electrode to ablate tissue is based at least in part on measurements from the plurality of sensors.

15. The method of claim 13, further comprising determining contact of the at least one electrode with the tissue based on measurements from the at least one contact force sensor assembly.

16. The method of claim 13, further comprising estimating a degree of contact of the at least one electrode with the tissue based on measurements from the at least one contact force sensor assembly.

17. A system for the ablation of a portion of tissue comprising:
    a catheter, wherein the catheter comprises:
        an elongated body;
        at least one ring electrode disposed on an intermediate portion of the elongated body;
        at least one contact force sensor assembly operably connected to the at least one ring electrode, the at least one contact force sensor assembly comprising a strain gauge, the strain gauge having a radius of curvature that is complementary to an interior wall of the at least one ring electrode, and a detent operably attached to the strain gauge, the detent being disposed within and extending through a correspondingly shaped opening in a wall of the at least one ring electrode; and
        a plurality of irrigation apertures formed in the wall of the at least one ring electrode; and
    a system controller capable of receiving signals from a plurality of sensors and delivering power to the at least one ring electrode and controlling the power to the at least one ring electrode to ablate tissue.

18. The system of claim 17, wherein the system controller is further configured to receive signals from the at least one contact force sensor assembly to indicate the degree of contact of the at least one electrode to the tissue to be ablated.

* * * * *